United States Patent [19]

Kosak

[11] Patent Number: 4,760,187

[45] Date of Patent: Jul. 26, 1988

[54] PROCESS FOR REDUCING CHLORONITROBENZENES USING RUTHENIUM WITH A MINOR AMOUNT OF PLATINUM AS THE CATALYST

[75] Inventor: John R. Kosak, Greenville, Del.

[73] Assignee: E. I. Du Pont de Nemours and Company, Wilmington, Del.

[21] Appl. No.: 60,967

[22] Filed: Jun. 17, 1987

Related U.S. Application Data

[63] Continuation-in-part of Ser. No. 695,855, Jan. 25, 1985, abandoned, which is a continuation-in-part of Ser. No. 293,010, Aug. 14, 1981, abandoned.

[51] Int. Cl.$^4$ ............... C07C 85/11; C07C 87/60; C09B 107/06
[52] U.S. Cl. ................... 564/417; 534/585; 534/839; 564/418; 564/422; 564/423; 564/442
[58] Field of Search ............... 564/417, 418, 422, 423, 564/442

[56] References Cited

U.S. PATENT DOCUMENTS

| | | | |
|---|---|---|---|
| 3,361,819 | 2/1968 | Kosak et al. | 564/417 X |
| 3,832,401 | 8/1974 | Knifton et al. | 564/417 X |
| 4,005,143 | 1/1977 | Bohm et al. | 564/418 |
| 4,059,627 | 11/1977 | Kritzler et al. | 564/417 |
| 4,070,401 | 1/1978 | Hirai et al. | 564/417 |
| 4,164,481 | 8/1979 | Ma et al. | 564/412 |
| 4,169,853 | 10/1979 | Knifton | 564/417 |

FOREIGN PATENT DOCUMENTS

| | | | |
|---|---|---|---|
| 1064959 | 4/1967 | United Kingdom | 564/417 |
| 188982 | 11/1966 | U.S.S.R. | 564/417 |

OTHER PUBLICATIONS

Bennett, Concise Chemical and Technical Dictionary, p. 482 (1947).
Rylander et al, Actes Second Congr. Internat. Katal (Paris 1960) Ed Technik, pp. 977 to 985 (1961).
Sokolova et al, N. D. Zelinski, Inst. of Org. Chem. Acad. Sci. USSR, pp. 1830–1833 (1966).

*Primary Examiner*—Floyd D. Higel
*Attorney, Agent, or Firm*—Craig H. Evans

[57] ABSTRACT

A process for reducing chloronitrobenzenes to the corresponding chloroanilines using a combination ruthenium-platinum catalyst is disclosed. The ratio of ruthenium to platinum in the catalyst is from 75:1 to 30:1. The pressure used is from 200 to 800 psi with from 400 to 600 psi being the preferred range. The temperature used is from 70° to 160° C. with from 110° to 150° C. being the preferred range.

11 Claims, No Drawings

PROCESS FOR REDUCING CHLORONITROBENZENES USING RUTHENIUM WITH A MINOR AMOUNT OF PLATINUM AS THE CATALYST

CROSS-REFERENCE TO RELATED APPLICATION

This application is a continuation-in-part of application Ser. No. 695,855, filed Jan. 25, 1985, now abandoned, which is a continuation-in-part of Ser. No. 293,010, filed Aug. 14, 1981, now abandoned.

BACKGROUND OF THE INVENTION

1. Field of the Invention

The present invention relates to a process of reducing chloronitrobenzenes to the corresponding chloroanilines.

2. Description of the Prior Art

Russian Pat. No. 188,982 and "Catalytic Reduction of Chloronitrobenzenes to Chloroanilines" by N. P. Sokolova et al. N. D. Zelinskii Institute of Organic Chemistry, Academy of Sciences of the USSR, pp 1830–1833 (1966) translated from Izvestiya Akademii Nauk SSSR, Seriya Khimicheskaya, No. 11, pp 1891–1895, November 1966, disclose the use of ruthenium supported on barium sulfate as the catalyst for reducing chloronitrobenzene to chloroaniline at pressures of 50 atm. and 100 atm. and temperatures up to 90° C.

Br. 1,064,959 discloses the hydrogenation of halonitrobenzene to haloaniline using a sulfide of platinum, rhodium, ruthenium or palladium as the catalyst. The use of platinum metal catalyst as the control runs is also disclosed.

U.S. Pat. No. 4,164,481 discloses the regeneration of noble metal catalysts which have been used to hydrogenate nitrobenzene to aniline.

U.S. Pat. No. 4,059,627 discloses the hydrogenation of chloronitrobenzene to chloroaniline in the presence of a sulfur compound such as a thioether.

U.S. Pat. No. 4,169,853 discloses the use of solubilized ruthenium-containing complexes in combination with quaternary ammonium hydroxides to effect the reduction of various ortho-substituted nitroaromatics.

Rylander et al., Actes Second. Congr. Interna. Kaltal., Paris (1960), Ed. Technip., Paris (1961), pages 977–985 disclose the reduction of nitrobenzene using ruthenium, platinum, and ruthenium-platinum catalysts.

BACKGROUND AND SUMMARY OF THE INVENTION

In order to have a safe and efficient process for the hydrogen reduction of chloronitrobenzenes to corresponding chloroanilines, the rate of reaction should be as high as possible and dechlorination and coupling side reactions should be avoided or minimized.

Dechlorination has long been recognized as the major source of yield loss, that is, the lowering of the theoretical weight percent conversion to chloroaniline based on the starting weight of chloronitrobenzene.

Coupling has less of an effect on conversion but does result in the formation of chloroazobenzene which is an acnegen known to cause health and safety problems for workers if present at too high a level.

Furthermore, if high levels of the chloroazobenzene are formed in the process, the crude chloroaniline must be fractionally distilled to remove the chloroazobenzene prior to shipment of the product chloroaniline. This results in yield losses that can be substantial and added cost of waste handling. Also since chloroazobenzene will concentrate in the waste, health hazards are increased particularly when connecting and disconnecting waste trailers which are generally used to transport waste trailers to be incinerated. By minimizing the coupling reaction and the resulting formation of chloroazobenzene in the crude chloroaniline, less distillation and handling of waste is needed. Thus, overall yield and safety are improved. Preferred levels of chloroazobenzene in the crude chloroaniline are less than 1000 parts per million (ppm) and in the final product are less than 100 ppm.

To prevent dechlorination when using platinum as a catalyst, dechlorination suppressors or inhibitors such as morpholine have been required. Alternatively, a highly selective catalyst such as ruthenium can theoretically be used. But, the rate of reaction when using ruthenium alone is too slow for efficient operation. Rate of reaction when using ruthenium alone can be increased by operating at pressures above 1000 psi but this adds cost associated with having to use higher pressure equipment.

Rate of reaction is known to be good when employing platinum as a catalyst, but substantial dechlorination results if a dechlorination suppressor is not used. A detrimental amount of the chloroazobenzene is formed even with the use of the dechlorination suppressor. U.S. Pat. No. 3,361,819 discloses the need to maintain the amount of chloronitrobenzene in the reaction mixture between 1 and 50 weight percent to prevent formation of detrimental amounts of the chloroazobenzene.

It has now been found that, when reducing chloronitrobenzenes to the corresponding chloroanilines, the small addition of a supported platinum catalyst to a predominantly supported ruthenium catalyst will significantly increase the rate of hydrogenation at pressures less than 1000 psi without having a significant effect on the normally high selectivity associated with ruthenium. Also, the production of chloroazobenzene normally associated with platinum is kept to within preferred limits. Dechlorination suppressors are not required and the concentration of chloronitrobenzene in the reaction mixture need not be controlled when the ruthenium with a small amount of platinum is used.

DETAILED DESCRIPTION

In accordance with the present invention reduction of a chloronitrobenzene to its corresponding chloroaniline involves introducing elemental hydrogen, or equivalent source of hydrogen, into a reaction mixture containing the halonitrobenzene and a suitable quantity of catalyst. Generally from 0.1 to 5.0 percent by weight catalyst including ruthenium, platinum and support, as based on the chloronitrobenzene, will be used. Preferably, the reaction is performed in the liquid phase and to this end temperatures and pressures which admit of a liquid phase are used.

Further it is preferred to perform the reaction at a temperature which not only permits a liquid phase reaction, but also which favors most efficient conversion with respect to rate of reaction, byproduct formation and minimum dechlorination. In this regard, temperatures from about 70° C. to 160° C. are operable with 110° C. to 150° C. constituting the best range. At temperatures above about 160° C. the desired conversion takes place, but the product is contaminated with by-products. Below 70° C., the reaction rate is such that prolonged reaction periods are required in order to obtain an economical degree of conversion.

Generally the pressure should be from 200 to 800 psi with from 400 to 600 being the preferred range. Above about 800 psi the expense of creating the pressure becomes excessive with little gain in reactivity. Below about 200 psi the reaction rate becomes excessively slow.

The catalyst will generally contain from 0.5 to 10 wt. % ruthenium as based on the total amount of catalyst and catalyst support present. Generally the ratio of ruthenium to platinum present in the catalyst will vary from 75:1 to 30:1 with from 60:1 to 30:1 being the preferred range. The ruthenium and platinum may be present on the same catalyst support or the two metals may be separately supported and the two catalysts co-mixed in the reactor. The ruthenium and platinum catalyst may be prepared in various ways in order that a large surface area of metallic ruthenium or platinum per unit weight thereof is provided. A typical preparation includes depositing metallic ruthenium or platinum, as by spraying, saturating, or precipitating a salt followed by reduction or the like, on a finely divided inert support such as activated alumina or activated carbon. Generally the support will have a particle size of less than 200 mesh. Other suitable supports include finely divided silicon dioxide, calcium silicate, sodium silicate, mixed silicates such as calcium-aluminum silicate, calcium-sodium silicate, etc., talc, calcium carbonate, clay, etc.

Generally the reaction time will be from 20 to 300 minutes. The reaction may be run in either the batch or continuous mode.

The process does not require a dechlorination suppressor such as morpholine and is preferably run without one. There is no need to control the concentration of the chloronitrobenzene in the reaction mixture and preferably the concentration is not controlled. This permits starting the reaction with 100 percent chloronitrobenzene, catalyst and hydrogen in the reactor.

While the process of the present invention is generally applicable to any chloronitrobenzene, the chloronitrobenzenes containing one to three chlorine atoms and one nitro group are preferred. The preferred chloronitrobenzenes are 1-nitro-3,4-dichlorobenzene, 1-nitro-2-chlorobenzene, 1-nitro-4-chlorobenzene, 1-nitro-2,5-dichlorobenzene and 1-nitro-2,3-dichlorobenzene.

The process of the present invention minimizes production of the chloroazobenzene corresponding to the nitrochlorobenzene starting material. 3,3′,4,4′-tetrachloroazobenzene is an acnegen, and, therefore, its production is undesirable.

The chloroanilines produced by the process of the present invention are useful as intermediates in the production of herbicides, dyes and pigments.

DESCRIPTION OF THE PREFERRED EMBODIMENTS

In each of Examples 1-13 as reported in Table I a one-liter titanium autoclave is charged with 300 g of nitrodichlorobenzene containing 86.3% of the 1 nitro-3,4-dichlorobenzene isomer and 1.2 g of a commercial 5 wt. % ruthenium on finely divided carbon catalyst. The platinum catalyst (Pt-Cat) used in Examples 1-11 is a commercial 5 wt. % platinum on finely divided carbon catalyst. The platinum catalyst used in Examples 12 and 13 contains 5 wt. % platinum, 1.25 wt. % nickel and 1.25 wt. % chromium supported on finely divided carbon, prepared by the process of U.S. Pat. No. 3,546,297. In each of Examples 1-13 the autoclave is pressured to 500 psig (3450 kPag) and repressured to 500 psig (3450 kPag) whenever the pressure drops to 400 psig (2760 kPag). In control Examples 1 and 2 a higher temperature of 140°/150° C. is used which effectively doubles the reaction rate obtained when 130°/140° C. is used. In Table I "DECHL" stands for dechlorination, "DCA" stands for the 3,4-dichloroaniline product and "TCAB" stands for 3,3′,4,4′-tetrachloroazobenzene. The "DCA" yields reported in Table I are based on the 1-nitro-3,4-dichlorobenzene in the starting material.

| Ex. | Pt-Cat. g | Time Min. | Temp. °C. | DECHL % | DCA % | TCAB PPM |
|---|---|---|---|---|---|---|
| 1 | 0 | 225 | 140/150 | 0.52 | 97.1 | — |
| 2 | 0 | 255 | 140/150 | 0.825 | 96.8 | — |
| 3 | 0.02 | 165 | 130/140 | 0.827 | 96.3 | — |
| 4 | 0.02 | 163 | 130/140 | 0.711 | 95.6 | — |
| 5 | 0.03 | 105 | 130/140 | 0.786 | 96.8 | 217 |
| 6 | 0.03 | 106 | 130/140 | 0.689 | 97.0 | 64 |
| 7 | 0.04 | 72 | 130/140 | 1.051 | 96.0 | 15 |
| 8 | 0.04 | 97 | 130/140 | 0.704 | 96.5 | 483 |
| 9 | 0.04 | 89 | 130/140 | 0.486 | 95.8 | 96 |
| 10 | 0.05 | 56 | 130/140 | 0.742 | 95.5 | 2830 |
| 11 | 0.05 | 58 | 130/140 | 1.056 | 96.3 | 2953 |
| 12 | 0.1 | 67 | 130/140 | 0.405 | 97.8 | 1346 |
| 13 | 0.1 | 66 | 130/140 | 0.383 | 98.0 | 2725 |

I claim:
1. A process of reducing chloronitrobenzenes to the corresponding chloroanilines comprising contacting said chloronitrobenzene with hydrogen without the addition of a dechlorination suppressor at from 70° C. to 160° C. and a pressure of from 200 to 800 psi in the presence of a catalytic amount of supported metallic ruthenium and supported metallic platinum wherein the weight ratio of ruthenium to platinum is from 75:1 to 30:1.

2. The process of claim 1 wherein the catalyst is supported on a finely divided inert carrier said ruthenium comprising from 0.5 to 10 weight percent of the carrier.

3. The process of claim 2 wherein the catalyst including ruthenium, platinum and support is present in an amount of from 0.1 to 5.0 percent by weight as based on the chloronitrobenzene starting material.

4. The process of claim 3 wherein the chloronitrobenzene starting material contains from 1 to 3 chlorine atoms and one nitro group.

5. The process of claim 4 wherein the temperature is from 110° to 150° C.

6. The process of claim 5 wherein the weight ratio of ruthenium to platinum is from 60:1 to 30:1.

7. The process of claim 6 wherein the pressure is from 400 to 600 psi.

8. The process of claim 7 wherein the chloronitrobenzene starting material is selected from the class consisting of 1-nitro-3,4-dichlorobenzene, 1-nitro-2-chlorobenzene, 1-nitro-4-chlorobenzene, 1-nitro-2,5-dichlorobenzene, and 1-nitro-2,3-dichlorobenzene.

9. The process of claim 8 wherein the catalyst support is selected from the class consisting of carbon black and alumina.

10. The process of claim 1 wherein the chloronitrobenzene is contacted with hydrogen without control of concentration of chloronitrobenzene.

11. The process of claim 10 wherein the weight ratio of ruthenium to platinum is from 60:1 to 30:1.

* * * * *